United States Patent
Blehaut et al.

(10) Patent No.: US 6,325,898 B1
(45) Date of Patent: Dec. 4, 2001

(54) CONSTITUENT SEPARATION SYSTEM

(75) Inventors: Jean Blehaut, Nancy; Roger-Marc Nicoud, Richardmesnil, both of (FR)

(73) Assignees: Institut Francais du Petrole, Rueil-Malmaison Cedex; NOVASEP, Vandoeuvre-les-Nancy Cedex, both of (FR)

( * ) Notice: Subject to any disclaimer, the term of this patent is extended or adjusted under 35 U.S.C. 154(b) by 0 days.

(21) Appl. No.: 09/357,138

(22) Filed: Jul. 20, 1999

(30) Foreign Application Priority Data

Jul. 24, 1998 (FR) .................................................. 98 09540

(51) Int. Cl.[7] ...................................................... B01D 3/42
(52) U.S. Cl. ............................... 202/160; 202/181; 203/1; 203/2; 203/3; 203/DIG. 18; 210/201; 210/96.2; 210/198.2; 210/294; 210/266
(58) Field of Search ..................... 203/1, 2, 3, DIG. 18, 203/89; 202/181, 236, 160; 435/803; 159/44, DIG. 3, 13.1; 210/96.2, 198.2, 201, 656, 294, 266

(56) References Cited

U.S. PATENT DOCUMENTS 3,998,704 * 12/1976 Follain et al. ........................ 202/160
4,877,522   10/1989 Toei et al. .
5,464,504 * 11/1995 Beauford ................................. 203/3
5,522,660    6/1996 O'Dougherty .

FOREIGN PATENT DOCUMENTS 754491    1/1997 (EP) .

* cited by examiner

Primary Examiner—Virginia Manoharan
(74) Attorney, Agent, or Firm—Antonelli, Terry, Stout & Kraus, LLP

(57) ABSTRACT

A device allows for continuous regulation of the composition of a fluid mixture that includes at least two components of different polarities. The device is designed, for example, to be inserted in a separation system that the device supplies with a carrier fluid of stabilized composition. The device includes a storage tank (3) receiving a mixture coming from the separation system and at least one auxiliary vessel (6) containing one of the components of the mixture. To control the transfer of this component from auxiliary vessel (6) to storage tank (3), the device further includes at least one tubular capacitive sonde (CS) totally immersed in the fluid mixture, a sonde (TS) for measuring the temperature of the mixture, and a sonde (LS) for measuring the mixture level in storage tank (3). A regulating unit (10) is connected to the various sondes to determine the volume of the component to be transferred to storage tank (3) from the at least one auxiliary vessel in order to restore a set composition for the mixture. The device can be used, for example, for the control of simulated moving beds, of distillation columns, etc.

14 Claims, 4 Drawing Sheets

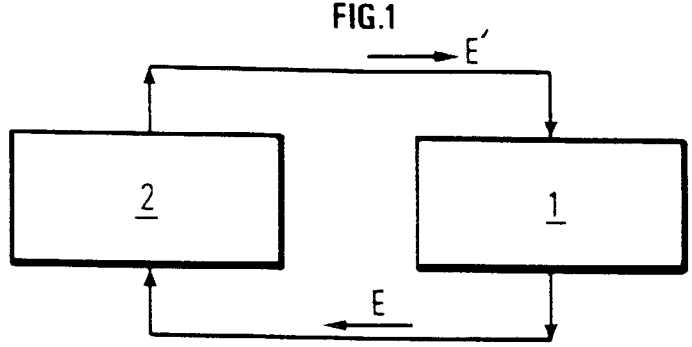
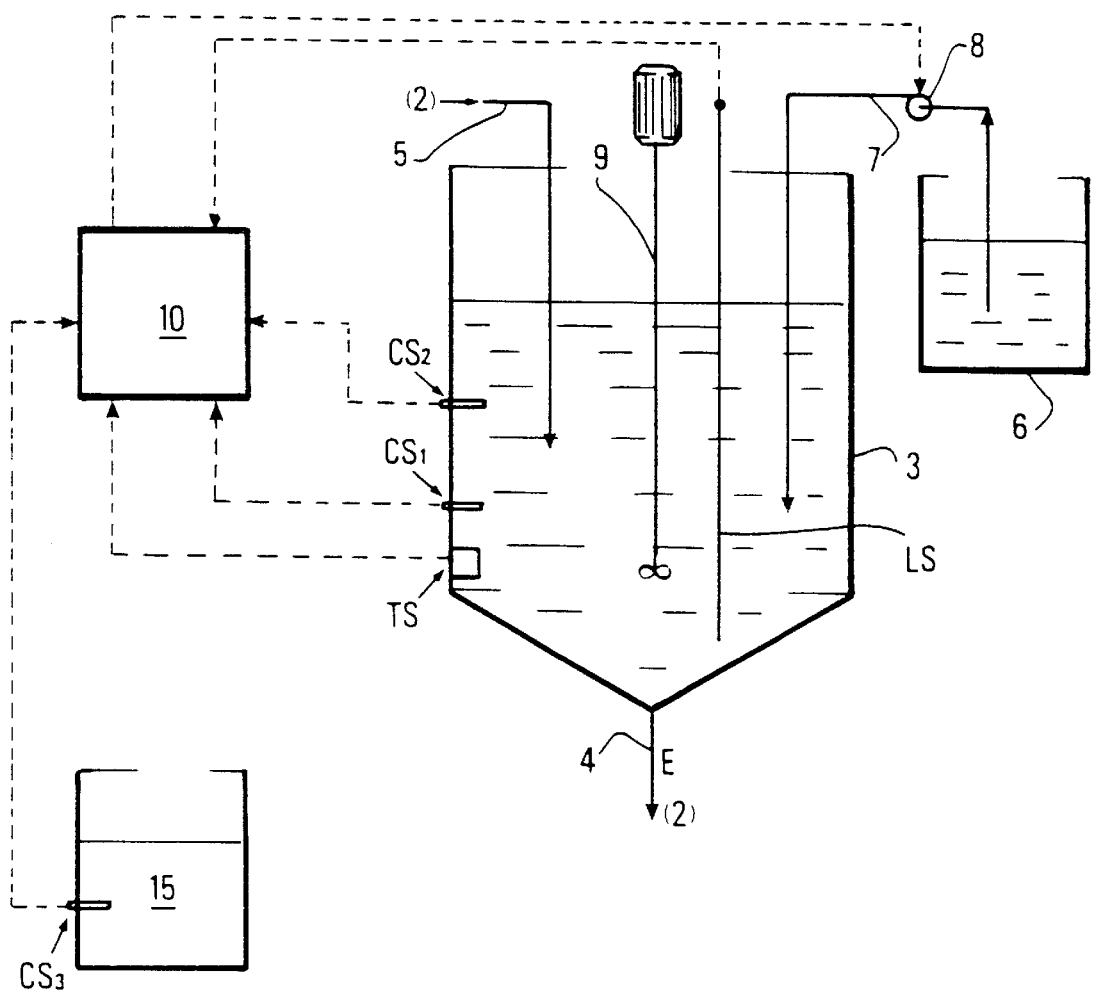

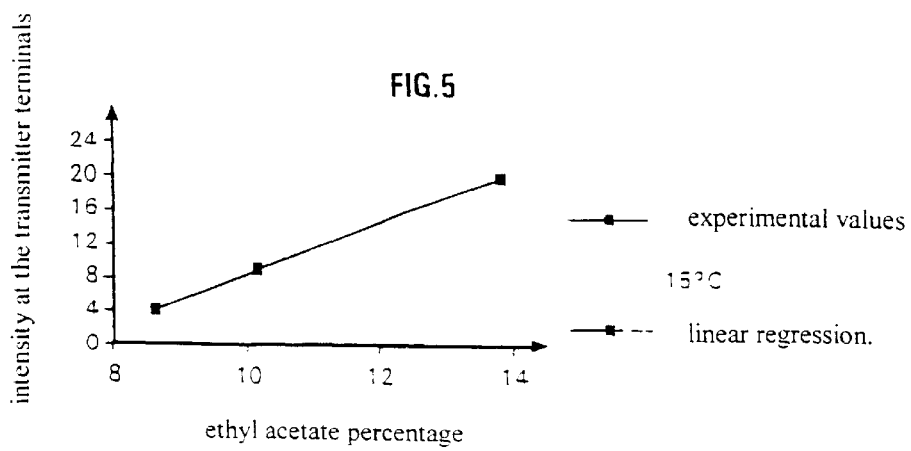
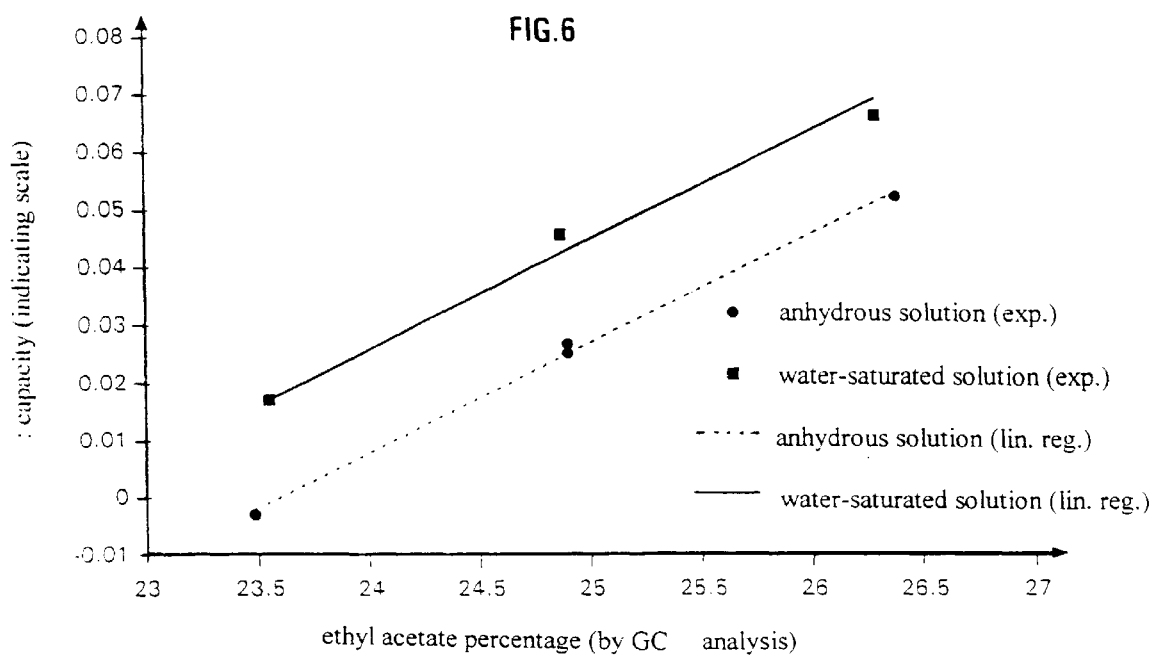
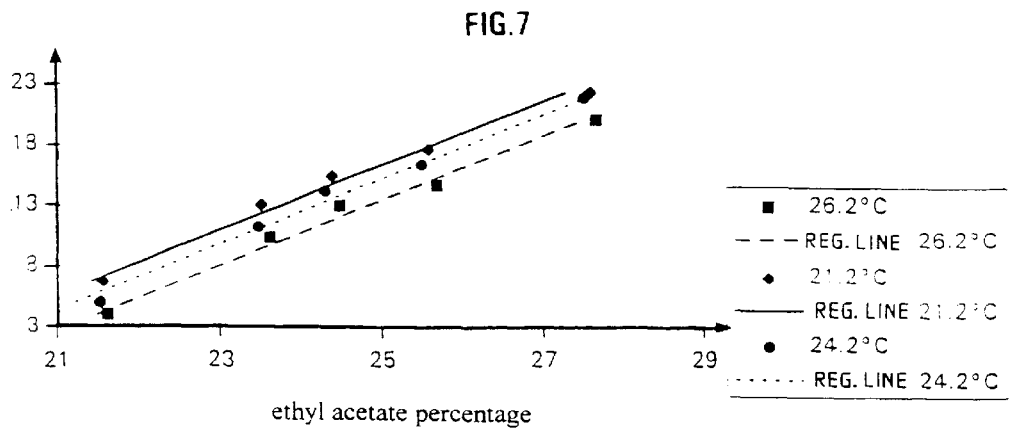

CONSTITUENT SEPARATION SYSTEM

FIELD OF THE INVENTION

The present invention relates to a device intended for continuous regulation of the composition of a binary mixture of components, and to a constituent separation system including this regulating device.

The regulating device according to the invention finds many applications. It can be used individually for homogeneity control of liquid mixtures, or it can be combined notably:
- with separation systems referred to as simulated moving bed systems,
- with separation systems referred to as "batch" systems of preparative HPLC type for example,
- with distillation columns for on-line analysis of the composition of the distillate or of the boiler and to optimize control of batch binary distillation processes,
- with separation systems comprising one or more nanofiltration membranes.

BACKGROUND OF THE INVENTION

There are many well-known continuous separation processes in industry using selective adsorption of at least one component among several in a mixture of fluids, notably chromatography processes referred to as simulated counter-current processes using the property of porous solids, in the presence of liquid, gaseous or supercritical mixtures, to retain more or less significantly the various constituents of the mixture.

Separation or fractionation processes based on chromatography are most often implemented in a system comprising a series of columns or fractions of columns interconnected in series and forming a loop. A porous solid of determined grain size constitutes the stationary phase. The mixture F to be separated is fed into the loop, then displaced by means of a carrier fluid, eluent E, and the various constituents flow out successively according to whether they are retained more or less significantly by the stationary phase. Injection points for the mixture F to be separated and the solvent or eluent E, and fluid extraction points, for extract EX and raffinate RA, delimiting different zones, are distributed along this loop. The number of zones can vary but the separation systems most often comprise four main zones.

In simulated moving bed separation processes, the solid phase is placed in a certain number n of fixed beds (generally $4 \leq n \leq 24$) arranged in series and it is the concentration profile that is displaced at a substantially uniform speed around a closed loop by successive shift of the injection and extraction points by means of a rotary valve or more simply of a series of suitably controlled on-off valves. This circular shifting, at each period T, of the various liquid inflows-outflows in a given direction allows to simulate displacement of the solid adsorbent in the other direction. The main liquid inflows are the flow of feed F and the flow of eluent S. According to the configuration selected, according to whether a recycling pump is used or not in the cycle, the outflows of extract EX or of raffinate RA can be controlled by the pressure at the inlet of the recycling pump or by means of flowmeters.

Simulated moving bed chromatography processes are for example described in patents EP-0,415,822; 0,568,407; FR-2,699,917; 2,704,158, and in patent applications FR-97/05,485 or 97/07,756.

In industrial chromatography processes, one of the main parameters allowing selective adsorption of the species to be separated and/or their solubility in the eluent is the polarity of the eluent. Most often, the eluent allowing optimum productivity of the process is a binary mixture of two solvents of different polarities.

For good stability of the working point of the loop, it is important that the fluid mixture (eluent) used as a carrier fluid for the constituents of the feed in the separation loop has a well-defined composition, where the proportion of each solvent remains really constant. Now, the eluent is generally recycled by evaporation and/or distillation at the outlet of the separation system. The solvents forming the eluent often have different volatilities. In the case of non-ideal mixtures in the presence of an azeotrope, the composition of the eluent may also be different from that of the azeotrope. The composition of the mixture recycled after use is consequently modified. It is therefore necessary to restore the set composition and to be able to perform continuous measurement of its variations.

SUMMARY OF THE INVENTION

The separation system according to the invention comprises a separation unit (simulated moving beds, distillation column, etc) and a device for supplying the separation unit with a mixture of liquids consisting of at least two components of different polarities.

The system is characterized in that the supply device comprises a storage tank receiving a mixture coming from the separation system, at least one auxiliary vessel containing one of the components of the mixture. and means for controlling transfer of this component from the auxiliary vessel to the storage tank, these means comprising at least a capacitive sonde totally immersed in the fluid mixture, a sonde for measuring the temperature of the mixture, a sonde for measuring the mixture level in the storage tank, and a regulating unit connected to the various sondes and suited to determine the volume of at least one of the components to be transferred to the storage tank, in order to restore a set composition for the mixture.

Immersed capacitive sondes suited to generate a current depending on the instantaneous composition of the mixture of components and on the temperature are preferably used, and the regulating unit is suited to determine the volume of at least one of the components of the mixture according to the instantaneous composition of the mixture, the set composition, the volume of the mixture in the tank and the composition of at least one makeup component.

The system preferably comprises stirring means in the storage tank and means associated therewith in order to maintain the temperature of the mixture substantially constant.

According to an embodiment, the system comprises a capacitive reference sonde immersed in a liquid mixture of known composition (obtained for example by mixing the same components) and maintained at a constant temperature, and the regulating unit is suited to regulate the composition of the mixture in the storage tank by reference to the intensity of the current delivered by said reference sonde.

It is notably possible to use immersed capacitive sondes comprising an elongate central electrode surrounded by an earth electrode that can be tubular and preferably open-worked in order to allow better circulation of the mixture through the inter-electrode space, and a generator producing a current proportional to the variations of the inter-electrode capacity.

The separation unit comprises, for example, a loop for separating the constituents of a feed, that is connected to the supply device and comprises means for injecting the feed into the separation loop and means for separating from the liquid mixture the constituents extracted from the feed.

According to an embodiment, the system comprises auxiliary feed preparation vessels and circuits for connecting the outlet of the tank to the auxiliary vessels on demand.

The separation unit can comprise, according to circumstances, a simulated moving bed unit or a distillation column or one or more chromatographic columns for supercritical chromatography for example, or one or more nanofiltration membranes.

According to an embodiment, the separation unit comprises for example falling-film evaporation means and a condenser connected to the storage tank.

BRIEF DESCRIPTION OF THE DRAWINGS

Other features and advantages of the invention will be clear from reading the description hereafter of a non limitative realization example, with reference to the accompanying drawings wherein:

FIG. 1 illustrates the functional combination of the regulating device with a separation system, FIG. 2 diagrammatically shows the layout of the regulating device, FIG. 3 diagrammatically shows an example of immersed capacitive sonde for detecting composition variations of a mixture of fluids, FIG. 5 shows an example of calibration curve of variations of the intensity I delivered by an immersed capacitive sonde, as a function of the variation of the percentage of ethyl acetate (EA) in a mixture at 15° C. also containing heptane, FIG. 6 shows two variation curves of the inter-electrode capacity of the detection sonde (obtained by linear regression) as a function of the variation of the percentage of ethyl acetate (EA), curve A corresponding to an anhydrous mixture of solvents, curve B corresponding to a water-saturated mixture of solvents, FIG. 7 shows a variation curve (obtained by linear regression) of the intensity I delivered by the detection sonde as a function of the variation of the percentage of ethyl acetate (EA) in a mixture, for a temperature of 21.2° C. (curve A) and the corresponding measuring points for two other temperatures: 24.2° C. (curve B) and 26.2° C. (curve C)

DETAILED DESCRIPTION

Figure 4:
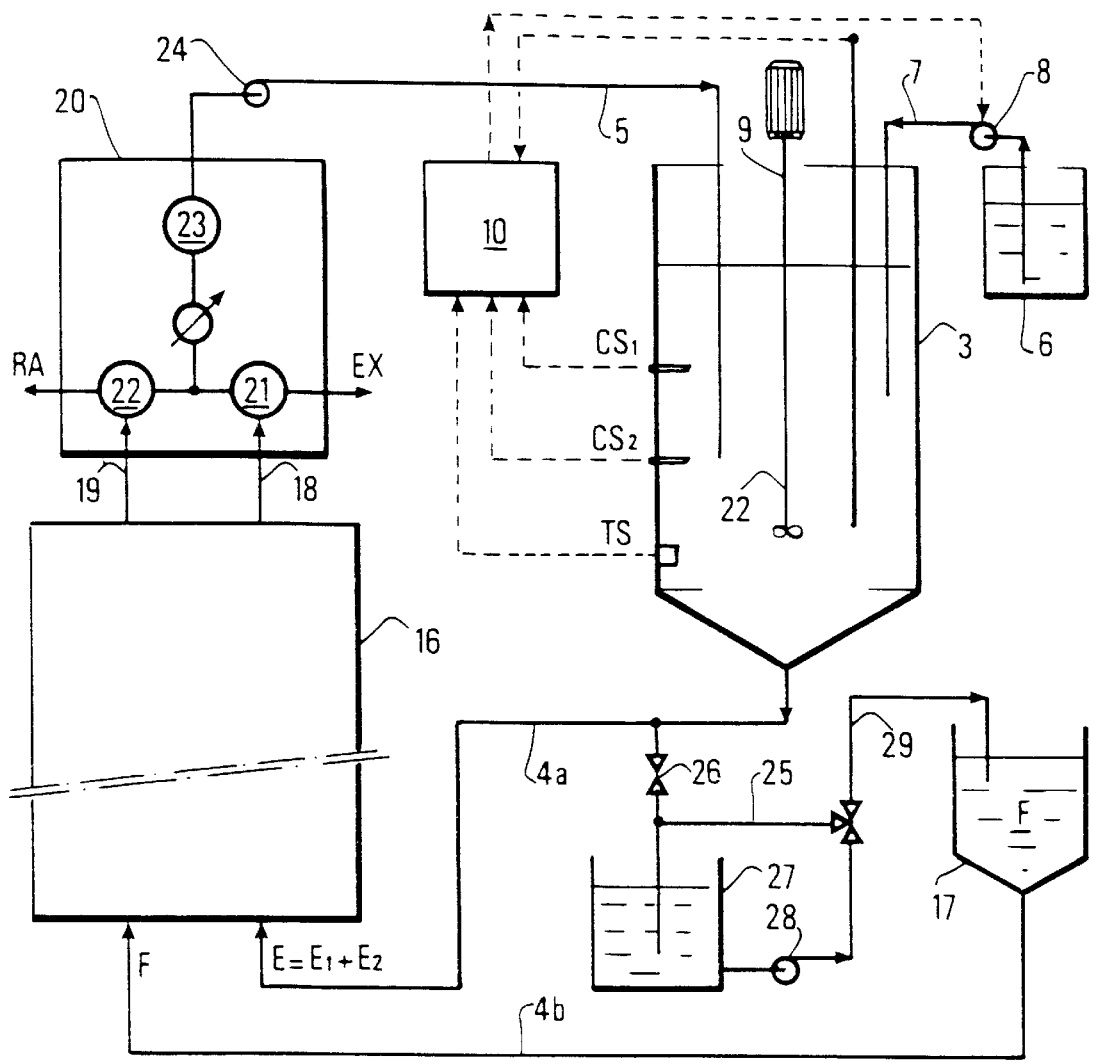
FIG. 4 shows the block diagram of an example of device for regulating the composition of a mixture, associated with a chromatographic system for separating the constituents.

Regulating device 1 (FIG. 1) can be associated, for example, in a constituent separation system 2. It supplies it with a fluid mixture E of regulated composition, consisting of at least two different substances E1, E2 and, after circulation in the separation system, a mixture E' is returned thereto, where the proportion of each constituent substance is generally different from that of regulated mixture E. It can be, for example, a system for separating the constituents of a feed where the fluid mixture consisting of at least two solvents of different volatilities is used as a carrier fluid for example.

Device 1 comprises (FIG. 2) a storage tank 3 for storing a fluid mixture E consisting for example of two solvents E1, E2, supplying the separation system through a line 4. Mixture E' is returned to the tank through line 5. In order to restore the initial proportion of the two solvents in the mixture, a reserve of the less volatile solvent (E2 for example) can be taken from an auxiliary tank 6 connected to tank 3 by a circuit 7, by means of a pump 8. A stirring device 9 homogenizes the mixture in tank 3. Pump 8 is selectively actuated by a control unit 10 according to the value of certain parameters measured by various measuring sondes associated with tank 3.

A first capacitive type sonde LS for example measures the mixture level in tank 3. A second sonde TS measures the temperature of the mixture. The composition of the mixture in tank 3 is permanently measured by at least one detection sonde CS1.

Figure 3:
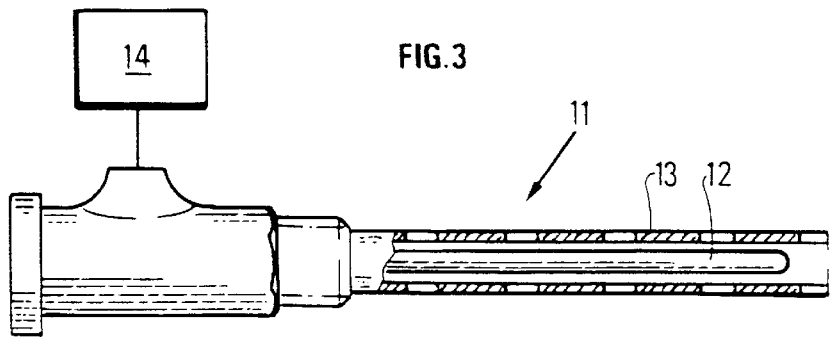

This sonde CS1 comprises for example an entirely immersed capacitive pickup 11 of a well-known type (FIG. 3) provided with a central electrode 12 surrounded by an earth electrode 13 that can be tubular and preferably openworked. This earth electrode can however consist of a conducting wall of tank 3. The inter-electrode capacity depending on the electric permittivity of the mixture and therefore on the respective permittivities of solvents E1, E2, the sonde is sensitive to the composition variations of the mixture. Pickup 11 is associated with a 4–20 mA type current generator or transmitter 14, that produces a current I depending on the composition of the mixture and on temperature T. The instantaneous composition $C_i$ of the mixture, that is a function $f_1$ of current I and of temperature difference $(T-T_0)$, where $T_0$ represents the reference temperature at which the sonde is calibrated, is deduced therefrom.

In a certain temperature and composition range, the variations of the intensity as a function of these two parameters can be approximated by means of straight lines and function f can be defined by:

$$C_i(T_0)=a.I+b,$$

according to a calibration at controlled temperature $T_0$, and $$C_i(T)=f_1(I,T)=C_i(I,T_0)+d=a.I+b+d.$$

Function $f_1$ is determined experimentally. The variations of the intensity delivered by sonde CS with the previous calibration temperature are taken into account. A second sonde CS2 identical to the first one can also be placed in the tank and allows to corroborate the measuring signals delivered by the first sonde.

The signals delivered by the various sondes or pickups LS, TS, CS1 and possibly CS2 are applied to control unit 10 that determines the volume ΔV of constituent to be taken from auxiliary tank 6 in order to regulate, around the set composition $C_c$, the composition Ci(t) of the eluent in tank 3. A programmed microprocessor is for example used to compute:

$$\Delta V=f_2(C_i, C_c, V_E, C_A),$$

where $C_A$ represents the composition of the makeup solvent.

Previous calibrations allow to determine the function $f_2$ to be applied, suitable for the experimental working conditions of the separation system as shown by the experimental curves of FIGS. 5 to 8.

The necessary corrective volume ΔV can be transferred by means of a constant-delivery pump 8 by playing on the duration of the time interval required for transfer of the solvent from vessel 6.

Figure 8:
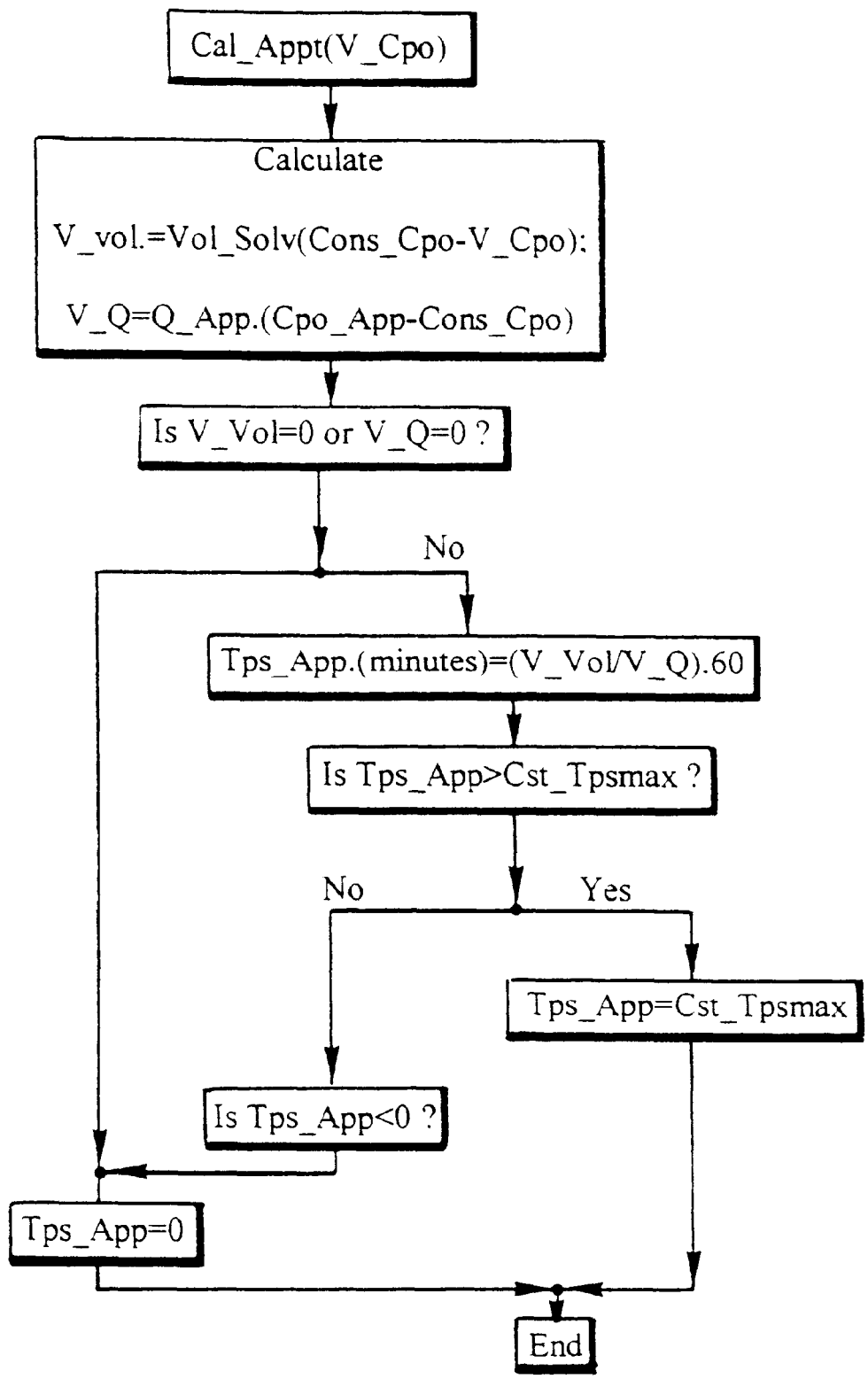
FIG. 8 shows a flowchart for calculating the supply of a component allowing to maintain the composition of the mixture.

In FIG. 8, that shows a flowchart for calculating the transfer time, the following symbols represent:

Q_App. is the delivery rate of the pump delivering the makeup volume (in l/h),

Cons_Cpo, the desired set composition of the mixture E of solvents,

Cpo_App, the composition of makeup solvent E2,

Vol_Solv, the volume of solvent measured in tank 3 (in litres),

Tps_App, the time interval for transfer of solvent E2, resulting from the calculation, and V_Cpo, the usual composition of mixture E.

According to a realization variant, a reference sonde CS3 (FIG. 2) immersed in a mixture of known composition (identical to set composition $C_i$ for example) and contained in a thermostat-controlled vessel 15 at a fixed temperature can also be connected to control unit 10, which facilitates discrimination of the current variations of sondes CS, specifically connected with variations in the composition of the mixture.

If control unit 10 detects variations in the composition of the mixture, it activates pumping of solvent E2 in auxiliary tank 6.

Regulating device 1, described above, can for example be combined (FIG. 4) with a separation system comprising a simulated moving bed separation loop 16 where mixture E is used as the eluent. Loop 16 comprises two inlets, a first inlet connected by circuit 4A to eluent tank 3 and a second inlet connected to a tank 17 containing a feed F by a circuit 4B. Loop 16 comprises two outlets connected by two circuits 18, 19 respectively to two inlets of a separation unit 20 intended to separate an extract EX on the one hand and a raffinate RA on the other from the flow of eluent.

This separation unit 20 comprises, for example, falling-film evaporators 21, 22 where the eluent is evaporated. The eluent vapours are collected in a condenser 23 and recycled to tank 3 via circuit 5 by means of a pump 24. Because of their different volatilities, the composition of eluent E' recycled to tank 3 is modified, which therefore requires regulation as explained above.

Eluent tank 3 is also connected by a circuit 25 provided with a control valve 26 to a feed preparation vessel 27 where the feed F to be injected into loop 16 is first mixed with the eluent. The prepared feed is transferred by means of a pump 28 and of a circuit 29 to feed storage tank 13.

What is claimed is:

1. A constituent separation system comprising a separation unit (2) and a supply device (1) for supplying the separation unit with a mixture of fluids comprising at least two components of different polarities, the supply device comprising a storage tank (3) for receiving a volume of the mixture coming from the separation unit, at least one auxiliary vessel (6) for one of the at least two components of the mixture, and an assembly for controlling a transfer of said one of the at least two components from the auxiliary vessel (6) to the storage tank (3), said assembly comprising at least a capacitive sonde (CS) totally immersed in the mixture of fluids, a sonde (TS) for measuring the temperature of the mixture, a sonde (LS) for measuring the mixture level in said storage tank (3), and a regulating unit (10) connected to the various sondes for determining the volume of said one of the at least two components to be transferred to storage tank (3), in order to restore a set composition for said mixture.

2. The constituent separation system of claim 1, wherein the immersed capacitive sonde (CS) generates a current depending on the instantaneous composition of the mixture of fluids and on the temperature, and the regulating unit (10) determines said volume of said one of the at least two components to be transferred to storage tank (3) according to an instantaneous composition of the mixture, a set composition, a volume of the mixture in the tank, and a composition of at least one makeup component.

3. The constituent separation system of claim 1 further comprising stirring means (9) in said storage tank (3) and means for maintaining the temperature of the mixture substantially constant therein.

4. The constituent separation system of claim 1, further comprising a capacitive reference sonde (CS3) immersed in a fluid mixture of known composition maintained at a constant temperature, the regulating unit (10) regulating the composition of the mixture in the storage tank (3) by reference to the intensity of the current delivered by said reference sonde.

5. The constituent separation system as claimed in claim 4, wherein the fluid mixture is obtained by mixing the same components as those of the mixture in storage tank (3).

6. The constituent separation system of claim 4, wherein the immersed capacitive reference sonde (CS3) comprises an elongate central electrode (12) surrounded by a tubular earth electrode (13), and a generator (14) for producing a current proportional to variations of a capacity between the central electrode and the tubular earth electrode.

7. The constituent separation system of claim 1, wherein the immersed capacitive sonde (CS) comprises an elongate central electrode (12) surrounded by a tubular earth electrode (13), and a generator (14) for producing a current proportional to variations of a capacity between the central electrode and the tubular earth electrode.

8. The constituent separation system of claim 1, wherein the separation unit includes a separation loop (16) for separating the constituents of a feed (F), connected to the supply device, means (17) for injecting feed (F) into the loop and means (20) for separating from the fluid mixture the constituents extracted from feed (F).

9. The constituent separation system of claim 8 wherein the means (20) comprises falling-film evaporation means (21, 22) and a condenser (23) connected to the storage tank (3).

10. The constituent separation system of claim 1 further comprising auxiliary vessels (17, 27) for preparing feed (F) and circuits (25, 26) for connecting the outlet of tank (3) to said auxiliary vessels on request.

11. The constituent separation system of claim 1 wherein the separation unit (2) is a simulated moving bed unit.

12. The constituent separation system of claim 1 wherein the separation unit (2) is a distillation column.

13. The constituent separation system of claim 1 wherein the separation unit (2) comprises at least one chromatographic column.

14. The constituent separation system of claim 1 wherein the separation unit (2) comprises at least one nanofiltration membranes.

* * * * *